(12) United States Patent
Liu et al.

(10) Patent No.: US 7,219,536 B2
(45) Date of Patent: May 22, 2007

(54) SYSTEM AND METHOD TO DETERMINE OIL QUALITY UTILIZING A SINGLE MULTI-FUNCTION SURFACE ACOUSTIC WAVE SENSOR

(75) Inventors: James Z T Liu, Belvidere, IL (US); Michael L. Rhodes, Richfield, MN (US); Aziz Rahman, Sharon, MA (US)

(73) Assignee: Honeywell International Inc., Morristown, NJ (US)

( * ) Notice: Subject to any disclaimer, the term of this patent is extended or adjusted under 35 U.S.C. 154(b) by 148 days.

(21) Appl. No.: 11/119,870

(22) Filed: Apr. 29, 2005

(65) Prior Publication Data
US 2006/0243032 A1   Nov. 2, 2006

(51) Int. Cl.
*G01N 29/36* (2006.01)
(52) U.S. Cl. .................. 73/54.24; 73/10; 73/54.25; 73/54.41; 73/64.53
(58) Field of Classification Search .............. 73/10, 73/32 A, 53.05, 54.01, 54.02, 54.23–54.27, 73/54.38, 54.41, 64.53
See application file for complete search history.

(56) References Cited

U.S. PATENT DOCUMENTS

| | | | |
|---|---|---|---|
| 4,691,714 A | 9/1987 | Wong et al. ............... 128/738 |
| 4,782,332 A | 11/1988 | Cipris et al. .............. 340/603 |
| 4,792,791 A | 12/1988 | Cipris et al. .............. 340/603 |
| 5,235,235 A | 8/1993 | Martin et al. ........... 310/313 D |
| 5,274,335 A | 12/1993 | Wang et al. ............... 324/689 |
| 5,301,643 A | 4/1994 | Garcyalny ............... 123/198 D |
| 5,336,396 A | 8/1994 | Shetley ..................... 210/90 |
| 5,519,330 A * | 5/1996 | Yamauchi et al. ......... 324/700 |
| 5,869,763 A | 2/1999 | Vig et al. ................. 73/580 |
| 5,878,708 A | 3/1999 | Ruman .................. 123/196 M |
| 6,023,961 A | 2/2000 | Discenzo et al. |
| 6,044,332 A | 3/2000 | Korsah et al. ............. 702/76 |
| 6,076,406 A | 6/2000 | Blair et al. ................ 73/590 |

(Continued)

OTHER PUBLICATIONS

Dickert et al., "QCM and SAW Transducers Allow Analyte Detection from Nanometer- to Micrometer-Dimensions Using Imprinting Techniques", 2001 IEEE International Frequency Control Symposium and PDA Exposition, pp. 528-534.*

(Continued)

*Primary Examiner*—Hezron Williams
*Assistant Examiner*—David A. Rogers
(74) *Attorney, Agent, or Firm*—Kermit D. Lopez; Luis M. Ortiz; William B. Shelby (57) ABSTRACT

A method and system for detecting oil quality. The quality of engine oil can be determined utilizing an acoustic wave sensor to obtain viscosity and corrosivity data associated with the engine oil. The acoustic wave sensor is coated with a material that selectively reacts to at least one type of an acid in order to provide data indicative of the presence of the acids in the engine oil. The etch rate or the corrosivity of the engine oil can be determined based on the frequency data obtained as a result of the frequency measurement utilizing the acoustic wave sensor. The viscosity of the engine oil can additionally be obtained based on a measurement of phase and amplitude obtained from the data utilizing the acoustic wave sensor. The etch rate and the viscosity measurement provide data indicative of the quality of the engine oil.

15 Claims, 4 Drawing Sheets

U.S. PATENT DOCUMENTS

| | | | |
|---|---|---|---|
| 6,260,408 B1 * | 7/2001 | Vig et al. | 73/64.53 |
| 6,293,136 B1 | 9/2001 | Kim | 73/19.03 |
| 6,508,100 B2 | 1/2003 | Berndorfer | 73/1.02 |
| 6,513,365 B1 * | 2/2003 | Bruetting et al. | 73/32 A |
| 6,557,396 B2 | 5/2003 | Ismail et al. | 73/53.05 |
| 6,776,024 B2 | 8/2004 | Jakoby | 73/10 |
| 6,786,080 B2 | 9/2004 | Jakoby et al. | 73/54.01 |
| 6,799,458 B2 | 10/2004 | Ismail et al. | 73/304 C |
| 7,178,378 B2 * | 2/2007 | Crawley et al. | 73/24.06 |
| 2004/0035398 A1 | 2/2004 | Klugl et al. | 123/456 |
| 2004/0123644 A1 | 7/2004 | Jakoby et al. | |

OTHER PUBLICATIONS

Reindl et al., "SAW Devices as Wireless Passive Sensors", 1996 IEEE Ultrasonics Symposium, pp. 363-367.*

Hammond J.M. et al., An Acoustic Automotive Engine Oil Quality Sensor, 1997 IEEE International Frequency Control Symposium, p. 72-80.

* cited by examiner

SYSTEM AND METHOD TO DETERMINE OIL QUALITY UTILIZING A SINGLE MULTI-FUNCTION SURFACE ACOUSTIC WAVE SENSOR

TECHNICAL FIELD

Embodiments are generally related to sensing devices and components thereof. Embodiments also relate to oil filter detection. Embodiments additionally relate to bulk acoustic wave (BAW) components and other surface acoustic devices thereof.

BACKGROUND OF THE INVENTION

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, they are also used for chemical vapor detection. Acoustic wave sensors are so named because they use a mechanical, or acoustic, wave as the sensing mechanism. As the acoustic wave propagates through or on the surface of the material, any changes to the characteristics of the propagation path affect the velocity, phase and/or amplitude of the wave.

Changes in acoustic wave characteristics can be monitored by measuring the frequency, phase characteristics, Q value, insertion loss and input impedance of the sensor and can then be correlated to the corresponding physical quantity or chemical quantity that is being measured. Virtually all acoustic wave devices and sensors utilize a piezoelectric crystal to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the acoustic wave sensor. The chemically sensitive coating, however, significantly reduce the Q value, hence the performance of the sensor. In a practical sensor design, the acoustic wave sensor is preferred to be as simple as possible (in electrode configurations, layers of electrode, coatings on top of the electrodes, etc).

Examples of acoustic wave sensors include acoustic wave detection devices, which are utilized to detect the presence of substances, such as chemicals, or environmental conditions such as temperature and pressure. An acoustical or acoustic wave (e.g., SAW/BAW) device acting as a sensor can provide a highly sensitive detection mechanism due to the high sensitivity to surface loading and the low noise, which results from their intrinsic high Q factor. Bulk acoustic wave devices are typically fabricated using a vacuum plater, such as those made by CHA, Transat or Saunder. The choice of the electrode materials and the thickness of the electrode are controlled by filament temperature and total heating time. The size and shape of electrodes are defined by proper use of masks. Surface acoustic wave devices are typically fabricated using photolithographic techniques with comb-like interdigital transducers placed on a piezoelectric material. Surface acoustic wave devices may have either a delay line or a resonator configuration.

Based on the foregoing, it can be appreciated that acoustic wave devices, such as a surface acoustic wave resonator (SAW-R), surface acoustic wave delay line (SAW-DL), surface transverse wave (STW), bulk acoustic wave (BAW), can be utilized in various sensing measurement applications. One of the primary differences between an acoustic wave sensor and a conventional sensor is that an acoustic wave can store energy mechanically. Once such a sensor is supplied with a certain amount of energy (e.g., through RF), the sensor can operate for a time without any active part (e.g., without a power supply or oscillator). This feature makes it possible to implement an acoustic wave device in an RF powered passive and wireless sensing application.

One promising application for micro-sensors involves engine oil quality sensors. Acoustic wave viscosity sensors have been tested in the context of oil quality sensors. While viscosity is a good indicator of many oil quality factors, including low temperature startability, fuel economy, thinning or thickening effects at high/low temperatures, lubricity, and oil film thickness in running automotive engines, viscosity is not an indicator of how much acid is present in engine oil. Such acids can cause a lot of damage to an automotive engine.

A certain percentage of engine oil is converted to acids and other unhealthy compounds. Theses acids can attack the engines by etching the engines. The truck automotive industry, for example, currently relies on engine oil's pH, TBN and TAN as indicators of oil quality, however, such methods do not provide direct indications of precisely how much acid is attacking the engine. Combining a viscosity and corrosivity monitor might provide a technique for solving this problem. Such a method, however, is very costly, time consuming and takes up a great deal of volume.

Based on the foregoing, it is believed that what is needed to overcome these problems involves the implementation of an etch rate (corrosivity) monitor in combination with viscosity measurements. It is believed that the oil quality monitoring methods and systems described herein can solve such conventional deficiencies.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensing device.

It is another aspect of the present invention to provide for an acoustic wave sensing device adapted for oil quality monitoring.

It is yet another aspect of the present invention to provide for an acoustic wave device that is coated with a material that is selectively reactive to acids in order to provide an acid etch rate (corrosivity) monitor thereof.

It is a further aspect of the present invention to provide for an acoustic wave device that is capable of measuring both the acid etch rate (corrosivity) and viscosity of engine oil.

The aforementioned aspects and other objectives and advantages can now be achieved as described herein. A method and system for detecting oil quality is disclosed herein. In general, the quality of engine oil can be determined utilizing an acoustic wave sensor to obtain amplitude/frequency data associated with the engine oil. The etch rate (i.e., acid etch rate or corrosivity) of the engine oil can also be determined based on the frequency data obtained as a result of the frequency measurement utilizing the acoustic wave sensor. The viscosity of the engine oil can additionally be obtained based on a measurement of phase and amplitude obtained from the acoustic wave sensor. The etch rate and the viscosity provide data indicative of the quality of the engine oil. The acoustic wave sensor is coated with a material that selectively reacts to at least one type of an acid in order to provide data indicative of the presence of the acids in the engine oil.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
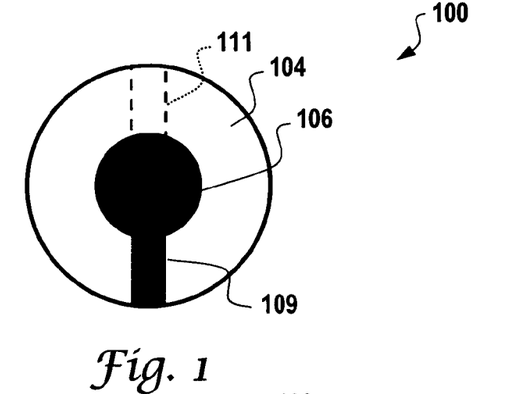
FIG. 1 illustrates a top view of a bulk wave device, which can be implemented in accordance with one embodiment.
Figure 2:
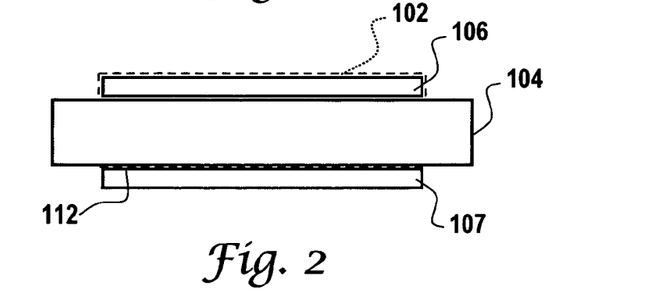
FIG. 2 illustrates a side view of the bulk wave device depicted in FIG. 1 in accordance with one embodiment.

FIG. 1 illustrates a top view of a bulk wave device 100, which can be implemented in accordance with one embodiment. FIG. 2 illustrates a side view of the bulk wave device 100 depicted in FIG. 1 in accordance with one embodiment. Note that in FIGS. 1-2, identical or similar parts are generally indicated by identical reference numerals. Bulk wave device 100 can be implemented in the context of a multiple function oil quality sensor. Bulk wave device 100 generally comprises two electrodes, including a top electrode 106 and a bottom electrode 107, which are formed on a piezoelectric substrate 104. The bulk wave device 100 can be implemented in the context of a sensor chip. The electrodes 106, 107 can be round or rectangular, depending upon design considerations. Note that the top electrode 106 can be provided with a top electrode connection 109 that can connect and/or communicate with another component, such as, for example, an antenna. Similarly, bottom electrode 107 can be provided with a bottom electrode connection 111 that can connect and/or communicate with another component, such as an antenna.

The bulk wave device 100 illustrated in FIG. 1 represents only one type of acoustic wave device or acoustic wave sensor that can be adapted for use with the embodiments disclosed herein. It can be appreciated that a variety of other types (e.g., APM, SH-APM, FPW, BAW, SAW-DL, SAW-R, etc.) can be utilized in accordance with the embodiments described herein. Additionally, bulk wave device 100 can be implemented in a variety of shapes (e.g., circular, square, diamond, rectangular, etc) and modes (e.g., fundamental and/or overtones).

A reactive coating film 102 depicted in FIG. 2 can be selected such that a particular species (acids, etc,) to be measured react with the coating 102, thereby altering the frequency of the bulk wave device 100. Various reactive coatings can be utilized to implement coating 102. A change in frequency can be detected and utilized to analyze how fast the metal is being attacked by the acids. Electrode 106 can therefore function as a reactive electrode when covered by coating 102. Please note that the electrode 106 and reactive film 102 could be the same, depending upon FEM considerations for the whole BAW device and the electrical and chemical properties of the materials used for the electrode 106 and reactive film 102. Thus, the bulk wave device is generally excited to implement a bulk acoustic mode. Such an excitation, however, can produce a variety of other modes of acoustic wave device 100.

Many modes of vibrations can exist in acoustic wave device 100. such as, for example, surface acoustic wave (SAW) and bulk acoustic wave (BAW) modes. Unlike, bulk wave device 100, most acoustic wave devices are designed such that only one mode of vibration is optimized, while other modes are suppressed. Such "undesired" mode(s), however, can be utilized for temperature compensation. Such modes can include, for example, flexural plate mode (FPM), acoustic plate mode, shear-horizontal acoustic plate mode (SH-APM), amplitude plate mode (APM), thickness shear mode (TSM), surface acoustic wave (SAW) mode, bulk acoustic wave mode (BAW), Torsional mode, love wave, leaky surface acoustic wave mode (LSAW), pseudo surface acoustic wave mode (PSAW), transverse mode, surface-skimming mode, surface transverse mode, harmonic modes, and/or overtone modes. Thus, in accordance with embodiments disclosed herein, multiple vibration modes (fundamental and overtones, etc) can be utilized to produce a temperature compensated multiple mode acoustic wave device, such as, bulk wave device 100.

Piezoelectric substrate 104 can be formed from a variety of substrate materials, such as, for example, quartz, lithium niobate (LiNbO$_3$), lithium tantalite (LiTaO$_3$), Li$_2$B$_4$O$_7$, GaPO$_4$, langasite (La$_3$Ga$_5$SiO$_{14}$), ZnO, and/or epitaxially grown nitrides such as Al, Ga or Ln, to name a few. Electrodes106 and 107 can be formed from materials, which are generally divided into three groups. First, electrodes 106, 107 can be formed from a metal group material (e.g., Al, Pt, Au, Ag, Rh, Ir, Zr, Cu, Ti, W, Cr, or Ni). Second, electrodes 106, 107 can be formed from alloys such as NiCr or CuAI. Third, electrodes 106, 107 can be formed from metal-nonmetal compounds (e.g., ceramic electrodes based on TiN, CoSi$_2$, or WC). A layer 112 can also be provided between electrode 107 and substrate 104 that functions, for example, as a Cr or Ti adhesion layer.

The reactive coating 102 acts as one electrode of the BAW device 100 and need not cover the entire planar surface of the piezoelectric substrate 104, but may cover only a portion thereof, depending upon design constraints. The size, shape and thickness of the reactive coating 102 determines BAW device 100 parameters such as motional resistance, equivalent circuit capacitance, Q value, spurs, harmonics, etc. This reactive film 102 and electrode 106 can cover part of the planar surface of piezoelectric substrate 104 depending upon FEM design constraints.

Because bulk wave device 100 functions as a multiple mode sensing device, excited multiple modes thereof generally occupy the same volume of piezoelectric material. Multiple modes excitation allows separations of temperature change effects from viscosity and corrosivity change effects. The multi-mode response can be represented by multiple mode equations, which can be solved to separate the response due to the temperature and viscosity, etc.

Figure 3:
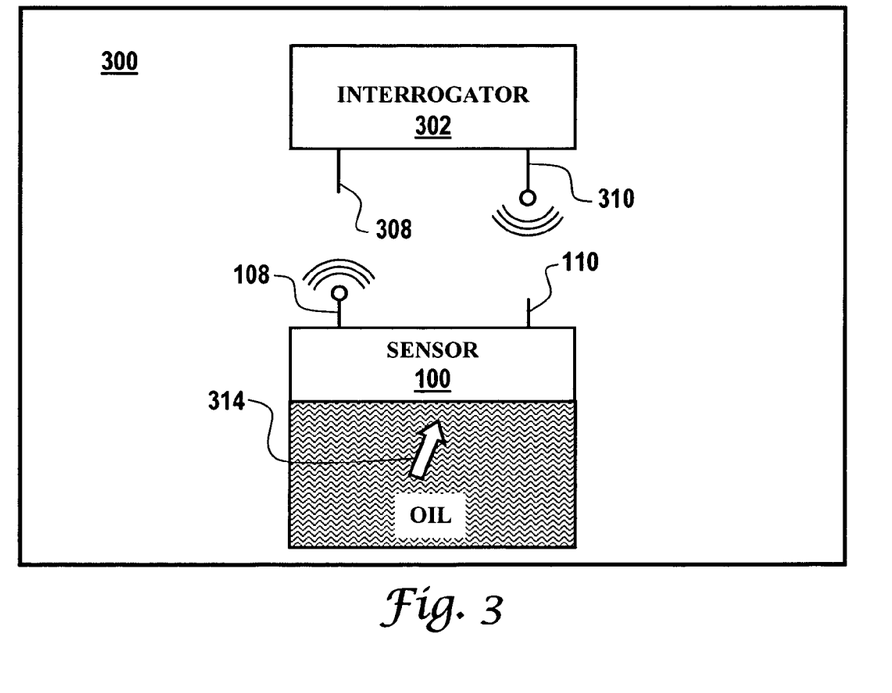
FIG. 3 illustrates a block diagram of a wireless and passive sensor system that can be implemented in accordance with a preferred embodiment.

FIG. 3 illustrates a block diagram of a wireless and passive sensor system 300 that can be implemented in accordance with a preferred embodiment. Note that in FIGS. 1-3, identical or similar parts or elements are generally indicated by identical reference numerals. Thus, the BAW device 100 depicted in FIGS. 1-2 functions as an oil quality sensor in accordance with the system 300 illustrated in FIG. 3. BAW device 100 can be implemented as an acoustic wave sensor equipped with antennas 108, 110.

As indicated by arrow 314 in FIG. 3, the surface of BAW device or sensor 100 can be exposed to oil. The acoustic wave sensor or BAW device 100 is excited by energy received through RF communications in order to vibrate in a desired mode(s) and transmit data back to an interrogator 302, which is equipped with antennas 308, 310. The acoustic wave sensor together with the antenna(s) act as a receiver, sensor and transmitter for system 300. The antennas 108 and 110 showing in the FIG. 3 act as transmitter and receiver, they can be the same one but function as both. Same as antennas 308 and 310.

Figure 4:
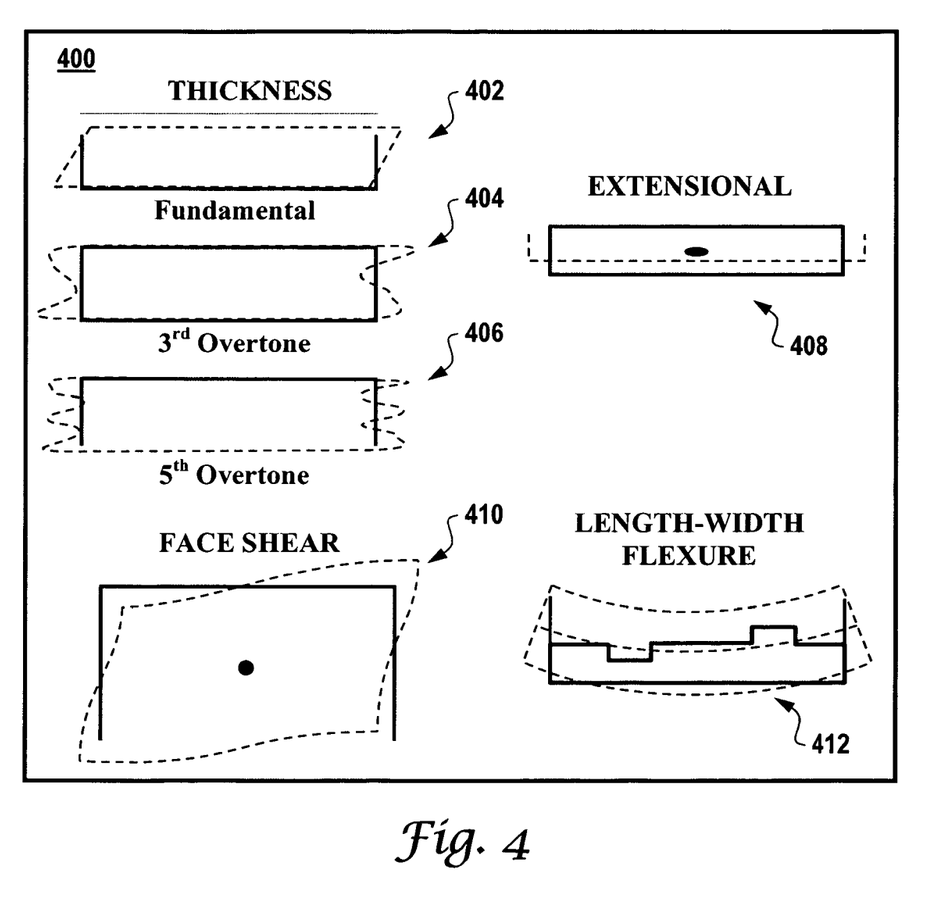
FIG. 4 illustrates multiple modes that can exist in a wireless oil sensor, in accordance with one embodiment.

FIG. 4 illustrates multiple modes 400 that can exist in a wireless oil sensor system as described herein. As indicated in FIG. 4, example modes 400 can include one or more thickness modes, including fundamental 402, $3^{rd}$ overtone 404, and $5^{th}$ overtone 406 modes. An extensional mode 408 is also depicted in FIG. 4, along with a face shear mode 410 and a length-width fixture mode 412. It can be appreciated that one or more of such modes can be adapted for use in accordance with one or more embodiments. Modes 400 depicted in FIG. 4 can therefore be considered in the implementation of an engine oil quality sensor.

Figure 5:
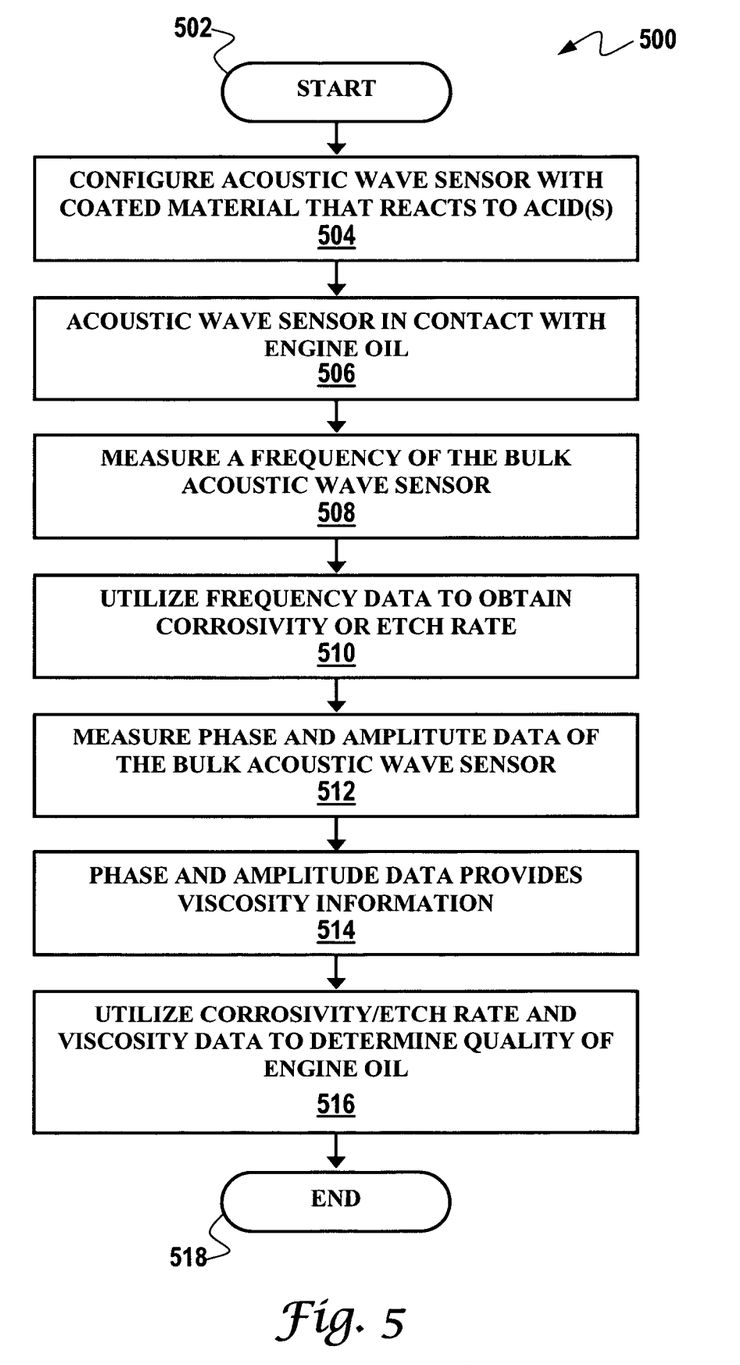
FIG. 5 illustrates a high-level flow chart of operations depicting logical operational steps that can be implemented in accordance with a preferred embodiment.

FIG. 5 illustrates a high-level flow chart 500 of operations depicting logical operational steps that can be implemented in accordance with a preferred embodiment. As indicated at block 502 of flow chart 500, the process can be initiated. First, as described at block 504, an acoustic wave sensor can be coated with a material that reacts to an acid. One example of such an acoustic wave sensor is, for example, BAW device 100 depicted in FIGS. 1-3. The methodology described herein with respect to FIG. 5 can also be implemented in the context of oil quality monitoring system 600 depicted in FIG. 6 herein.

Thus, the acoustic wave or BAW device 100 can be coated with a material that reacts to particular types of acids. Note that the bulk acoustic wave device can be implemented in the context of a wireless sensor (e.g., see antennas 108, 110 in FIG. 3). Coating 102 can thus be provided with a material property that is selectively reactive to acids.

As depicted thereafter at block 506, the acoustic wave sensor can come into contact with the engine oil. The sensor can be located, for example, in an oil filter or an internal combustion engine, to monitor the engine oil. Thereafter, as depicted at block 508, the frequency of the acoustic wave sensor can be measured. Next, as depicted at block 510, the corrosivity (e.g., etch rate) of the engine oil can be determined, based on the frequency obtained as a result of the frequency measurement utilizing the acoustic wave sensor.

Next, as depicted at block 512, a measurement of phase and amplitude can be obtained from the bulk acoustic wave sensor. Thereafter, as described at block 514, the phase and amplitude data can be utilized to compile viscosity information associated with the engine oil. Next, as depicted at block 516, the corrosivity/etch rate and the viscosity are utilized to provide data indicative of the quality of the engine oil. The process can then terminate as indicated at block 518.

By implementing the methodology depicted in FIG. 5, a single acoustic wave sensor can be implemented, which is capable of measuring both the etch rate and viscosity of engine oil. The etch rate is obtained through frequency measurement, as depicted at block 508, and the viscosity information can be obtained through phase and amplitude measurement as depicted at blocks 512 and 514. The reason the methodology depicted in FIG. 5 represents an ideal technique for measuring engine oil quality is that frequency is hardly influenced by viscosity and a very slow etch rate will not change the bulk wave phase and amplitude.

Note that when the etching electrode is coated with preferred materials simulating engine materials, these coated materials result in a mass loading effect on the base metal layer of the bulk acoustic wave sensing device and the QCM, but the electrical characteristics (R/L/C) are dominated by the base metal layer, the quartz surface roughness, etc. Viscosity appears as vibration resistance and contributes to amplitude changes. The bulk acoustic wave sensor may include, for example, one or more BAW electrodes formed thereon. In such a scenario, all such BAW electrodes can be exposed to the engine oil.

Thus, according to the methodology depicted in FIG. 5, an acoustic wave sensor can be coated with materials (i.e., or the entire electrode thereof) that are selectively reactive to particular types of acids and which can be utilized as an etch rate monitor and/or acid(s) monitor. The coating materials can be similar to those of engine materials. The most important difference between an acoustic wave device and a conventional wired sensor is that the acoustic wave device can store energy mechanically. Once the acoustic wave device is supplied with a certain amount of energy (e.g., through RF), the device can operation for a time without any active part (e.g., without power supply and/or oscillators). This feature makes it possible for an acoustic wave sensor to be implemented in the context of an RF powered passive and wireless sensing application.

Frequency changes of an acoustic wave device in viscosity measurement have been utilized in conventional applications. The frequency changes caused by small changes in viscosity of highly viscous liquids, however, are very small. Also, because of highly viscous loading, the signal from the oscillator is very noisy and the accuracy of conventional measurement systems is very poor. In the embodiments disclosed herein, however, phase and amplitude can be measured wirelessly (e.g., see antennas 108, 110, 308, 310 in FIG. 3).

Factors that influence the sensor properties include physical/chemical properties of the coating materials, coating thickness, coating modulus, coating morphology and bonding with the substrate. Such factors relate to coatings 102 described herein. An acoustic wave device is attractive to chemical detection applications because of their good linearity, short response time, small size, ruggedness, high sensitivity, low operating temperature and low power consumption.

The materials utilized to implement a coating, such as coating 102, will affect the sensor's selectivity. Though perfect selectivity for a single analyte is unattainable except for the biologically-based coating, adequate selectivity for a particular application can be obtained if the potential interferants are known. Coating structures and coating techniques therefore can affect the sensor's response to acids, and hence contribute to selectivity.

Quartz crystal resonators were originally developed for electronic oscillator components. In a typical etch rate monitor, however, the reaction of an acid with a selective thin film coating (e.g., applied to one surface of the crystal) or a reactive electrode can reduce the crystal's mass and increase its resonant frequency.

The frequency of a thickness shear mode (TSM) crystal unit, such as an AT-cut unit, is generally inversely proportional to the thickness of the crystal plate. For example, a typical 5 MHz $3^{rd}$ overtone plate is on the order of 1 million atomic layers thick. The etching of the coating/electrode equivalent to the mass of one atomic layer of quartz changes the frequency by about 1 ppm. Through calculations, one can see that the fundamental mode is 9 times more sensitive than that of the $3^{rd}$ overtone (i.e., see FIG. 5). A 5 MHz AT-cut TSM crystal blank, for example, is about 0.33 mm thick (fundamental). The thickness of the electrodes can be, for example, 0.2 to 0.5 µm. The change in frequency due to coating can therefore be demonstrated by the following formulation: $\delta F = -2.3 \times 10^6 F^2 (\delta M/A)$. In this case, the variable or value $\delta F$ represents the change in frequency due to the coating (Hz), and F represents the frequency of the quartz plate (Hz), $\delta M$ represents the mass of deposited coating (g), and A represents the area coated (cm$^2$).

Figure 6:
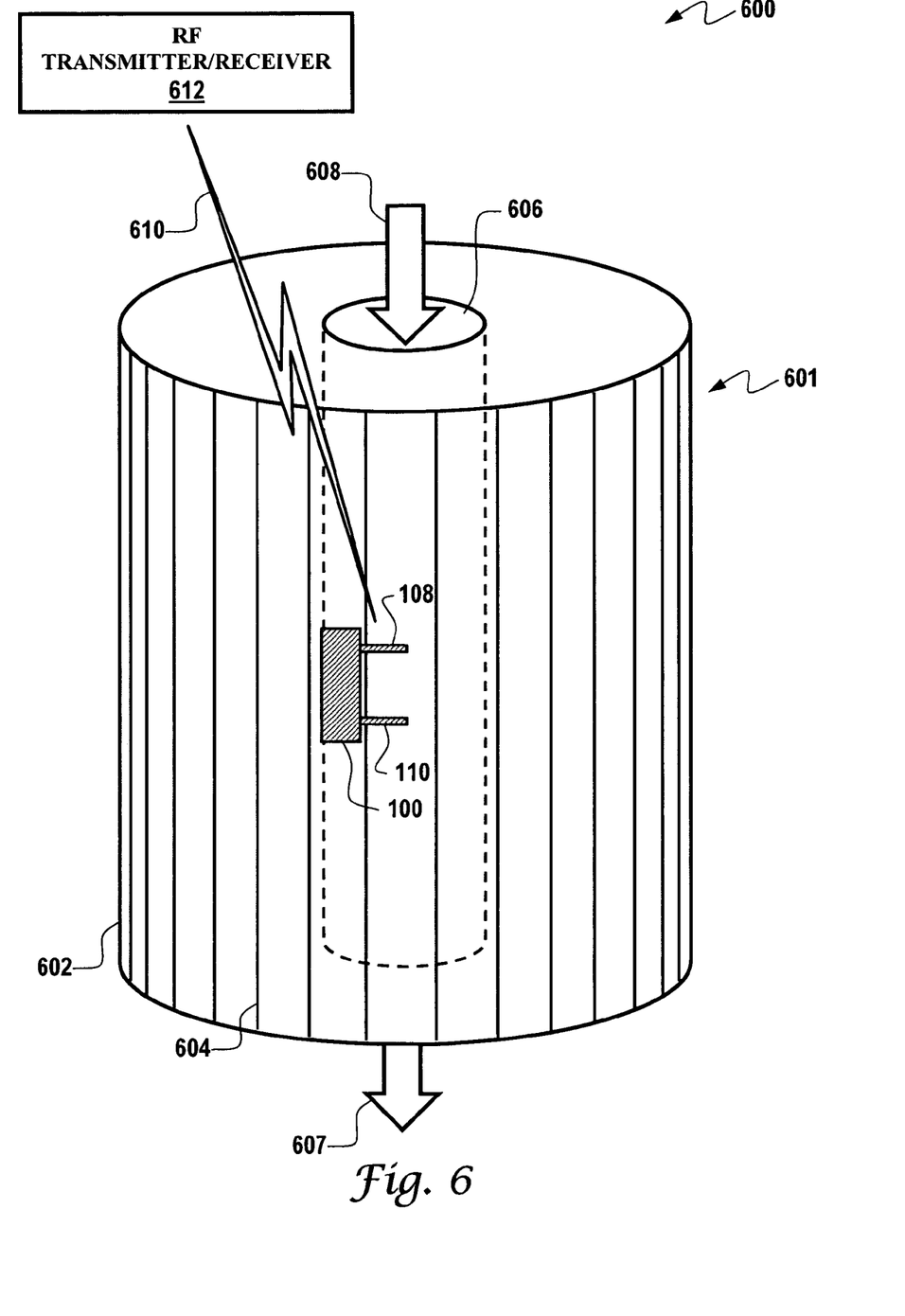
FIG. 6 illustrates a pictorial diagram of an oil quality monitoring system that can be implemented in accordance with an alternative embodiment.

FIG. 6 illustrates a pictorial diagram of an oil quality monitoring system 600 that can be implemented in accordance with an alternative embodiment. Note that in FIGS. 1-6, identical or similar parts or elements are generally indicated by identical reference numerals. System 600 generally includes an oil fitter 601 that includes an oil filter housing or canister 602 and oil filtration media 604. A gap 606 is centrally located in oil filter 601 through which engine oil flows as indicated by arrows 608 and 609. An acoustic wave sensor, such as BAW sensing device 100 with antennas 108, 110, can be located within gap 606 and transmit sensor data wirelessly to an RF transmitter/receiver 612, which may be located elsewhere (e.g. within an automobile cabin, an oil change station, an automotive shop, a home, garage, etc.). Note that RF transmit/receiver 612 generally functions as a wireless interrogator, such as, for example, interrogator 302 depicted in FIG. 3.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for detecting engine oil quality within an oil filter utilizing a single multi-function acoustic wave sensor, comprising:
    providing an acoustic wave sensor within said oil filter wherein said acoustic wave sensor is in contact with engine oil in said filter;
    coating at least one portion of said acoustic wave sensor with a reactive coating that selectively reacts to at least one type of an acid thereby causing a change in frequency data from said acoustic wave sensor over time;
    determining a corrosivity of said engine oil based on said frequency data obtained from said acoustic wave sensor; and
    obtaining a viscosity measurement of said engine oil based on measurements of phase and amplitude obtained utilizing said acoustic wave sensor, wherein said corrosivity and said viscosity measurements provide data indicative of the quality of said engine oil.

2. The method of claim 1 wherein said corrosivity measurement further comprises an etch rate.

3. The method of claim 1 further comprising providing an interrogator comprising a transmitter and a receiver and transmitting from said transmitter at least one signal in order to excite said acoustic wave sensor to vibrate in at least one desired mode thereof through at least one antenna integrated with said acoustic wave sensor.

4. The method of claim 3 further comprising receiving at said receiver at least one signal transmitted from said acoustic wave sensor.

5. The method of claim 1 further comprising providing at least one antenna connected to said acoustic wave sensor, such that said at least one antenna receives at least one excitation signal in order to permit said acoustic wave sensor to vibrate in at least one desired mode upon receipt of said excitation signals from an interrogator.

6. The method of claim 1 further comprising transmitting said frequency data from at least one antenna associated with said acoustic wave sensor, said data indicative of the quality of said engine oil to a receiver associated with an interrogator for receiving and collecting said data.

7. The method of claim 1 wherein said reactive coating comprises a material which simulates engine materials.

8. A system for detecting engine oil quality within an oil filter, comprising:
    an acoustic wave sensor for measuring frequency, phase and amplitude inside an engine oil filter in order to obtain viscosity and corrosivity data associated with said engine oil;
    a reactive coating covering at least one portion of said acoustic wave sensor, wherein said reactive coating selectively reacts to at least one type of an acid thereby causing a change in frequency data from said acoustic wave sensor over time;
    wherein a corrosivity measurement of said engine oil is determined based on said frequency data obtained as a result of measuring said quality of said engine oil utilizing said acoustic wave sensor; and
    wherein a viscosity measurement of said engine oil utilizing said acoustic wave sensor is based on said measurement of phase and an amplitude associated with said engine oil; and
    wherein said corrosivity and said viscosity measurement provide data indicative of the quality of said engine oil.

9. The system of claim 8 wherein said corrosivity measurement further comprises an etch rate.

10. The system of claim 8 further comprising providing an interrogator comprising a transmitter and a receiver.

11. The system of claim 10 wherein said interrogator further comprises a transmitter for transmitting at least one signal in order to excite said acoustic wave sensor to vibrate in at least one desired mode thereof through at least one antenna integrated with said acoustic wave sensor.

12. The system of claim 11 wherein said interrogator further comprises a receiver for receiving at least one signal transmitted from said acoustic wave sensor.

13. The system of claim 8 further comprising at least one antenna connected to said acoustic wave sensor, such said at least one antenna receives at least one excitation signal in order to permit said acoustic wave sensor to vibrate in at least one desired mode upon receipt of said excitation signals from an interrogator.

14. The system of claim 8 further comprising a transmitter for transmitting from at least one antenna associated with said acoustic wave sensor, said data indicative of the quality of said engine oil to a receiver associated with an interrogator for receiving and collecting said data.

15. The system of claim 8 wherein said reactive coating comprises a material which simulates engine materials.

* * * * *